United States Patent [19]

Simpkin et al.

[11] Patent Number: 5,188,841
[45] Date of Patent: Feb. 23, 1993

[54] SUSTAINED RELEASE PHARMACEUTICAL FORMULATIONS

[75] Inventors: Gordon T. Simpkin, Ingatestone, England; Isabelle Husson, Chevreuse, France

[73] Assignee: Rhone-Poulenc Sante, Antony, France

[21] Appl. No.: 539,193

[22] Filed: Jun. 18, 1990

[30] Foreign Application Priority Data

Jun. 16, 1989 [GB] United Kingdom ............... 8913889

[51] Int. Cl.$^5$ .............................................. A61K 9/16
[52] U.S. Cl. ................................. 424/495; 424/465; 424/466; 424/468; 424/469
[58] Field of Search ............... 424/495, 468, 466, 465, 424/469

[56] References Cited

U.S. PATENT DOCUMENTS 4,882,169 11/1989 Ventouras ..................... 424/495 X

FOREIGN PATENT DOCUMENTS 1561204 2/1980 United Kingdom .

Primary Examiner—Thurman K. Page
Assistant Examiner—William E. Benston, Jr.
Attorney, Agent, or Firm—Morgan & Finnegan

[57] ABSTRACT

The invention provides a sustained release formulation of ketoprofen comprising granules each of which comprises a core comprising ketoprofen and microcrystalline cellulose and a coating comprising a water-soluble and a water-insoluble cellulose derivative.

17 Claims, No Drawings

SUSTAINED RELEASE PHARMACEUTICAL FORMULATIONS

FIELD OF THE INVENTION

This invention relates to a sustained release pharmaceutical composition containing ketoprofen, and to a method for its production.

BACKGROUND OF THE INVENTION

Ketoprofen [2-(3-benzoylphenyl)propionic acid] is a nonsteroidal anti-inflammatory drug (NSAI) used in the treatment and control of a wide variety of conditions.

A number of formulations, including some sustained release, are known for this substance. Sustained release formulations are particularly suitable for NSAI's such as ketoprofen, as a single dose results in a therapeutic level of active material being maintained in the body for an extended period of time. There is however no generally applicable method for making such formulations and for each particular active material it is necessary to look at many criteria including rates of absorption, interactions with and between excipients, physical properties of active materials and of excipients, and bioavailability. Substantial experimentation must be undertaken in order to take into account such factors before a satisfactory formulation can be produced. It has now been found that, by using a particular combination of excipients, a new, useful, sustained release formulation of ketoprofen can be produced.

DETAILED DESCRIPTION OF THE INVENTION

The invention provides a sustained release formulation of ketoprofen, comprising granules, each of which comprises a core comprising ketoprofen and microcrystalline cellulose and a coating comprising a water-soluble and water-insoluble cellulose derivative.

The preferred insoluble and soluble components are ethylcellulose (EC) and hydroxypropylmethylcellulose (HPMC) respectively.

The core is preferable made by extrusion and is preferably spherical in form (produced, for example, by spheronization of an initially extruded body).

The proportion of ketoprofen to microcrystalline cellulose in the core is limited by the requirements of producing a stable core composition, capable of withstanding the coating process and any other necessary processing. There should also be sufficient ketoprofen present to limit the amounts of formulation to be administered to realistic levels. Ideally the amount of ketoprofen is 40 to 90, preferably 60 to 80, more preferably 75% (w/w).

A typical grade of microcrystalline cellulose that can be used is Avicel PH101.

The amount of coating applied is most readily defined in terms of the increase in weight of granules after coating. The preferred thickness depends on the precise nature of the coating and the required rate of release of the ketoprofen, but typically corresponds to a weight increase of 3 to 20, preferably 5 to 15, more preferably 10%.

EC is insoluble in water and HPMC is water soluble. Therefore adjusting the relative proportions of the two coating materials will alter the rate at which the ketoprofen passes through the coating by varying the numbers and sizes of the pores which are created by the dissolution of the soluble component in the digestive tract Clearly there must be a sufficient amount of the insoluble component to retard drug release, but a sufficient amount of the soluble component to allow passage of the ketoprofen through the coating at an acceptable rate after administration Hence the ratio of the insoluble to soluble components must be tailored to the particular formulation.

Use of too high a proportion of the insoluble EC will result in very thin coatings being needed to obtain reasonable rates of release. This coating is then liable to be non-discrete and non-continuous, and there is also the possibility of significant variation of thickness. Hence there will be a lack of control of drug diffusion through the coating. On the other hand, the use of too high a proportion of the soluble HPMC will preclude adequate retardation of drug diffusion, even at very high coating thicknesses.

These factors provide practical limits to the coating composition. Bearing these factors in mind, typical levels of EC in the coating are in the range 95 to 50, preferably 90 to 60, more preferably 80 to 70% (w/w).

It is also preferred for the EC to have an ethoxy group content of 40-55%, more preferably 43-51% (by weight).

Typical grades of EC that can be used are Ethocel E7 and Ethocel E10 and of HPMC are Pharmacoat 606 and Pharmacoat 615.

Conventional extra excipients, such as sodium carboxymethylcellulose, can be incorporated into the core during its formation. These typically account for less than 5% (w/w) of the core. Similarly, other conventional excipients can also be incorporated into the coating.

Typically the size of the granules is limited to a particular value or range, for example 0.5 to 2.0, preferably 0.8 to 1.4 mm.

A further coating (for example an enteric coating, such as hydroxypropylmethylcellulose phthalate) can also be applied, in a conventional manner, to the particles according to the invention.

The particles according to the invention can be made by mixing ketoprofen and microcrystalline cellulose, optionally in the presence of further excipients (such as sodium carboxymethylcellulose) and optionally in the presence of sufficient water to ensure adequate mixing and forming cores from this mixture, for example by extrusion and spheronization. These are dried if necessary, and a suitable size fraction is isolated. This fraction is coated (for example in a fluidized bed) using a solution of a mixture of the two polymers in the desired proportions in a suitable solvent (for example a mixture of methanol and dichloromethane).

In-vitro tests show that formulations according to the invention do show an extended, approximately linear release rate for ketoprofen at typical physiological pH's, indicating that they are able to sustain a therapeutic level of ketoprofen in the body over a period of time.

The formulations according to the invention may be used in the management of rheumatoid arthritis, osteoarthritis, ankylosing spondylitis, acute articular and periarticular disorders (bursitis, capsulitis, synovitis, tendinitis), fibrositis, cervical spondylitis, low back pain (strain, lumbago, sciatica, fibrositis), painful musculoskeletal conditions and dysmenorrhoea. They may be used, for example, to reduce joint pain and inflammation, and to facilitate increase in mobility and functional independence.

The typical daily dose for an adult would provide 50 to 500 mg, more particularly 100 to 200 mg, of ketoprofen, depending on the weight of the patient and the severity of the symptoms.

EXAMPLE

Ketoprofen (3 kg) and microcrystalline cellulose (Avicel PH101; 965.6 g) were thoroughly mixed in a planetary mixer. The resulting powder was granulated, over a period of 2 minutes, with a 1.5% (w/w) aqueous solution of sodium carboxymethylcellulose (Courlose) (2363 g). The resulting mixture was extruded to produce cylindrical pieces, 1 mm in diameter and 1 mm or more long, which were spheronized by treatment for 3 minutes at 500 rpm. The resultant spherical granules were dried at 40°-50° C. for 17 hours and the 0.8-1.4 mm fraction was separated out by sieving. The separated fraction was then coated with a freshly prepared 5% (w/w) solution of a 7:3 (w/w) mixture of EC (Ethocel E7 Premium) and HPMC (Pharmacoat 606) in a 1:1 (w/w) mixture of methanol and dichloromethane to produce the final product.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Granules, each of which comprises a core comprising ketoprofen and microcrystalline cellulose wherein the amount of ketoprofen is 60 to 80% w/w of the weight of the core and a coating comprising a water-soluble and a water-insoluble cellulose derivative wherein the coating comprises 90 to 60% w/w of ethylcellulose.

2. Granules according to claim 1 wherein the water-insoluble cellulose derivative is ethylcellulose.

3. Granules according to claim 1 wherein the water-soluble cellulose derivative is hydroxypropylmethylcellulose.

4. Granules according to claim 1 wherein the amount of ketoprofen is 75% w/w of the weight of the core and the coating comprises 80 to 70% w/w of ethyl cellulose.

5. Granules according to claim 1 wherein the weight of the coating comprises 3 to 20% of the weight of the core.

6. Granules according to claim 1 wherein the weight of the coating comprises 5 to 15% of the weight of the core.

7. Granules according to claim 1 wherein the weight of the coating comprises 10% of the weight of the core.

8. Granules according to claim 1 wherein the coating comprises from 90 to 60% w/w of ethylcellulose.

9. Granules according to claim 1 wherein the coating comprises from 80 to 70% w/w of ethylcellulose.

10. Granules according to claim 1 further comprising as the water-insoluble cellulose derivative ethylcellulose having an ethoxy group content of 40 to 55% by weight.

11. Granules according to claim 10 wherein the ethoxy group content is 43 to 51% by weight.

12. Granules according to claim 1 wherein the size of the granules is from 0.5 to 2.0 mm.

13. Granules according to claim 12, wherein the size is from 0.8 to 1.4 mm.

14. Granules according to claim 1 further comprising an enteric coating.

15. A process for the preparation of granules according to claim 1 comprising mixing ketoprofen and microcrystalline cellulose, forming cores from the mixture obtained wherein the amount of ketoprofen is 60 to 80% w/w of the weight of the core, if necessary drying the cores and isolating a desired size fraction, and forming on the cores a coating comprising a water-soluble and a water-insoluble cellulose derivative wherein the coating comprises 90 to 60% w/w of ethylcellulose.

16. A pharmaceutical composition comprising granules according to claim 1.

17. Granules according to claim 1 wherein the weight of the coating comprises 3 to 5% of the weight of the core.

* * * * *